United States Patent
De La Serna et al.

(10) Patent No.: US 10,064,798 B1
(45) Date of Patent: Sep. 4, 2018

(54) METHOD FOR MODULATING PIGMENTATION BY TARGETING BET BROMODOMAIN PROTEINS

(71) Applicant: The University of Toledo, Toledo, OH (US)

(72) Inventors: Ivana De La Serna, Toledo, OH (US); Archit Trivedi, Toledo, OH (US)

(73) Assignee: THE UNIVERSITY OF TOLEDO, Toledo, OH (US)

( * ) Notice: Subject to any disclaimer, the term of this patent is extended or adjusted under 35 U.S.C. 154(b) by 322 days.

(21) Appl. No.: 14/567,033

(22) Filed: Dec. 11, 2014

Related U.S. Application Data

(60) Provisional application No. 61/915,780, filed on Dec. 13, 2013.

(51) Int. Cl.
*A61K 8/49* (2006.01)
*A61Q 19/02* (2006.01)

(52) U.S. Cl.
CPC .............. *A61K 8/494* (2013.01); *A61Q 19/02* (2013.01); *A61K 2800/782* (2013.01)

(58) Field of Classification Search
None
See application file for complete search history.

(56) References Cited

PUBLICATIONS

Haq, Targeting melanoma by small molecules: challenges ahead, Pigment Cell Melanoma, Apr. 2013, 26, pp. 464-469.*

Filippakopoulos, Selective inhibition of BET bromodomains, Nature, 2010, 468, pp. 1067-1073.*
Halder, Topical Agents Used in the Management of Hyperpigmentation, Skin Therapy Letter, 2004, 9(6), pp. 1-4.*
Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
Stulberg, Common Hyperpigmentation Disorders in Adults: Part II. Melanoma, Seborrheic Keratoses,Acanthosis Nigricans, Melasma, Diabetic Dermopathy, Tinea Versicolor, and Postinflammatory Hyperpigmentation, 2003, American Family Physician, 68 (10), pp. 1963-1968.*
Haq, Targeting melanoma by small molecules: challenges ahead, Pigment Cell Melanoma, 2013, 26, pp. 464-469.*
Filippakopoulos et al., "Selective inhibition of BET bromodomains", Nature, 2010, vol. 468, No. 7327, pp. 1067-1073.

* cited by examiner

*Primary Examiner* — Kathrien A Cruz
*Assistant Examiner* — Andrew Lee
(74) *Attorney, Agent, or Firm* — MacMillan, Sobanski & Todd, LLC

(57) ABSTRACT

Methods, compositions, and kits useful for reducing pigmentation or treating hyperpigmentation disorders are disclosed. In accordance with the present disclosure, BET bromodomain protein inhibitors, such as JQ1, are used to reduce pigmentation, promote cell cycle arrest, inhibit the expression of TYR, TRP1, and DCT proteins, inhibit the expression of TYR mRNA, and suppress melanocyte proliferation.

15 Claims, 20 Drawing Sheets
(11 of 20 Drawing Sheet(s) Filed in Color)

METHOD FOR MODULATING PIGMENTATION BY TARGETING BET BROMODOMAIN PROTEINS

RELATED APPLICATIONS

This application claims priority to U.S. Provisional Application Ser. No. 61/915,780, filed under 35 U.S.C. § 111(b) on Dec. 13, 2013, the entire disclosure of which is incorporated herein by reference for all purposes.

STATEMENT REGARDING FEDERALLY SPONSORED RESEARCH

This invention was made with government support under Grant Number RO1 AR059379 awarded by the National Institutes of Health. The government has certain rights in this invention.

BACKGROUND OF THE INVENTION

Melanocytes are cells located in the basal layer of the epidermis that produce the pigment melanin. The melanocyte-specific enzyme, tyrosinase (TYR), is required for the rate-limiting step of melanin synthesis while two other members of the tyrosinase family, tyrosinase related protein 1 (TRP1) and dopachrome tautomerase (DCT), regulate the type of melanin synthesized. Once melanin is produced, it is stored in melanosomes, which are transferred from melanocytes to keratinacytes, thus giving skin its characteristic color. Disruption of normal melanocyte function can lead to skin cancer and other skin diseases that affect the level of pigmentation.

Hyperpigmentation is a common condition in which patches of skin become darker in color than the surrounding skin. Hyperpigmentation can affect the skin color of people of any skin tone. Possible causes of hyperpigmentation include pregnancy, Addison's disease, sun exposure, age, and certain drugs. Abnormal production of melanin can result in a number of hyperpigmentation disorders. As one example, melasma is a dysfunction of melanin production that results in irregular brown hyperpigmentation. Although the cause of melasma is not completely understood, common contributing factors include a genetic predisposition, dark complexion, pregnancy, use of oral contraceptives, endocrine disorders, hormone treatments, and exposure to ultraviolet light. In addition, some cosmetics and medications have also been linked to the development of melasma. As another example, solar lentigo is characterized by hyperpigmented lesions (sun spots) that range in size from a few millimeters to more than a centimeter in diameter and are associated with sun exposure. As another example, lentigo senilis (LS) is the skin condition of age spots characterized by enhanced epidermal pigmentation with an increase in the number of tyrosinase-positive melanocytes.

Because of their tendency to recur, hyperpigmentary conditions are often difficult to treat. Current treatment options for hyperpigmentation include chemical peels, laser resurfacing, intense pulse light therapy, and bleaching creams such as hydroquinone or arbutin. The use of topical hydroquinone is the most common treatment for many of these conditions. A predominant mechanism for the skin lightening effects of hydroquinone is through inhibition of tyrosinase activity. Chemical peels, laser treatments, and intense pulsed light therapy are additional therapeutic options. However, these options have adverse side effects such as skin irritation and hypopigmentation of surrounding skin. There is also concern about the safety of long term use of hydroquinone, which is a potential carcinogen. Thus, there is a need in the art for the development of additional and improved therapeutic options for hyperpigmentary conditions.

SUMMARY OF THE INVENTION

Provided herein is a method of reducing pigmentation in a skin cell comprising administering an effective amount of a BET bromodomain protein inhibitor to a skin cell to reduce pigmentation in the skin cell. In certain embodiments, the BET bromodomain protein inhibitor comprises JQ1. In particular embodiments, the JQ1 consists essentially of (+)-JQ1. In certain embodiments, pigment formation in melanocytes is reduced. In certain embodiments, pigment formation in melanocyte precursors is reduced. In certain embodiments, the skin cell is a melanoma cell.

Further provided is a method of treating a hyperpigmentation disorder comprising administering an effective amount of a BET bromodomain protein inhibitor to a patient in need thereof, and treating a hyperpigmentation disorder. In certain embodiments, the BET bromodomain protein inhibitor comprises JQ1. In certain embodiments, the hyperpigmentation disorder is selected from the group consisting of: melasma, lentigo senilis, solar lentigo, post-inflammatory hyperpigmentation, and ephelides. In certain embodiments, the administering comprises applying a topical composition to human skin. In certain embodiments, the method further comprises administering an additional treatment for a hyperpigmentation disorder, wherein the additional treatment is selected from the group consisting of: hydroquinone, azelaic acid, kojic acid, licorice extract, salicylic acid, glycolic acid, retinoic acid, retinol, 13-cis-retinoic acid, 9-cis-retinoic acid, corticosteroids, photoprotection agents, bakuchiol compositions, glutathione derivatives, and combinations thereof.

Further provided is a method of reducing tyrosinase (TYR) protein expression in a cell comprising administering an effective amount of a BET bromodomain protein inhibitor to a cell expressing TYR protein, and inhibiting TYR protein expression in the cell. In certain embodiments, the BET bromodomain protein inhibitor comprises JQ1.

Further provided is a method of reducing tyrosine related protein 1 (TRP1) expression in a cell comprising administering an effective amount of a BET bromodomain protein inhibitor to a cell expressing TRP1, and inhibiting TRP1 expression in the cell. In certain embodiments, the BET bromodomain protein inhibitor comprises JQ1.

Further provided is a method of reducing dopachrome tautomerase (DCT) protein expression in a cell comprising administering an effective amount of a BET bromodomain protein inhibitor to a cell expressing DCT, and inhibiting DCT expression in the cell. In certain embodiments, the BET bromodomain protein inhibitor comprises JQ1.

Further provided is a method of reducing TYR mRNA in a melanoblast comprising administering an effective amount of a BET bromodomain protein inhibitor to a melanoblast, and reducing TYR mRNA expression in the melanoblast. In certain embodiments, the BET bromodomain protein inhibitor comprises JQ1.

Further provided is a method of suppressing melanocyte proliferation comprising administering an effective amount of a BET bromodomain protein inhibitor to melanocytes, and suppressing proliferation of the melanocytes. In certain embodiments, the BET bromodomain protein inhibitor comprises JQ1. In certain embodiments, the melanocytes comprise melanoma cells.

Further provided is a pharmaceutical composition comprising a BET bromodomain protein inhibitor and a pharmaceutically acceptable carrier, where the composition is in the form of an ointment, cream, or lotion. In certain embodiments, the BET bromodomain protein inhibitor comprises JQ1.

Further provided is a kit for the treatment of hyperpigmentation comprising a first container housing a BET bromodomain protein inhibitor and a second container housing a pharmaceutically acceptable carrier, diluent, or excipient. In certain embodiments, the BET bromodomain protein inhibitor comprises JQ1.

BRIEF DESCRIPTION OF THE DRAWING

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

DETAILED DESCRIPTION OF THE INVENTION

Figure 1:
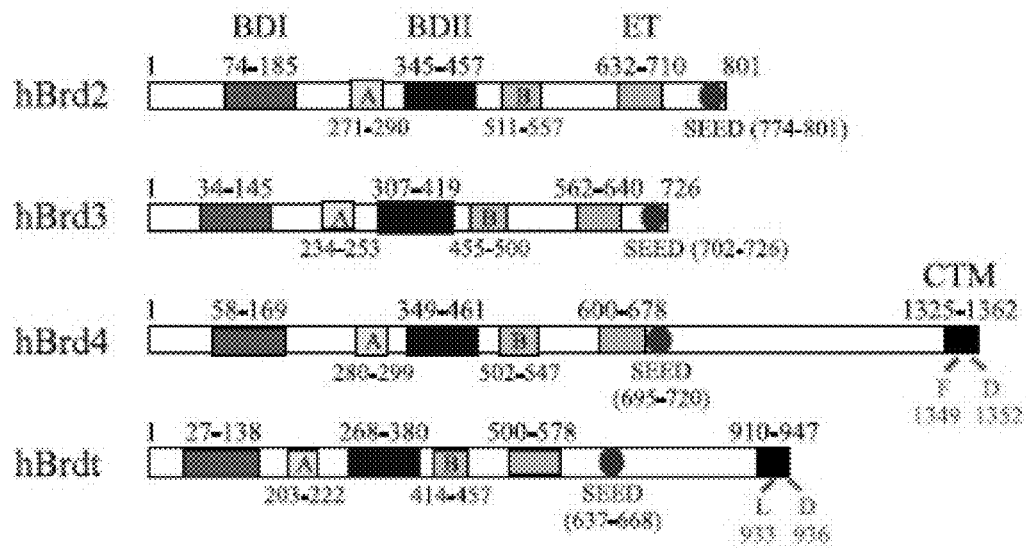
FIG. 1: The BET bromodomain and external domain family: BRD2, BRD3, BRD4, and BRDT.

Throughout this disclosure, various publications, patents, and published patent specifications are referenced by an identifying citation. The disclosures of these publications, patents and published patent specifications are hereby incorporated by reference into the present disclosure in their entirety to more fully describe the state of the art to which this invention pertains.

The microphthalmia-associated transcription factor (MITF) is an important regulator of pigmentation-specific genes and melanocyte proliferation. MITF is a helix-loop-helix leucine zipper transcription factor that binds to E box elements in the promoter region of the target genes. MITF is transcribed from several alternative promoters, giving rise to various splice isoforms.

MITF plays an important role in melanocyte differentiation. MITF is a master regulator of melanocyte differentiation that binds to the regulatory regions of many genes which regulate pigmentation, as well as genes important for melanocyte survival, and activates their expression. Thus, pharmacological suppression of MITF expression can decrease pigmentation. Modulation of MITF expression or activity is therefore a useful strategy for treating hyperpigmentation disorders.

MITF can interact with chromatin remodeling enzymes and thus promote changes in chromatin structure. Without wishing to be bound by theory, "epigenetic programming" through altered chromatin structure and histone modifications are believed to dictate how cells such as melanocytes specifically respond to certain environmental cues. Chromatin, the basic unit of which is the nucleosome, is formed by the wrapping of 146 base pairs of DNA around a core of four different histone proteins (H2A, H2B, H3, and H4). Post-translational modifications of histone proteins affect chromatin structure and gene expression. Histone post-translational modifications are regulated by enzymes with opposing activities that add or remove chemical groups from the amino termini of histone proteins. Acetylation of lysine residues on histone proteins is correlated with increases in chromatin accessibility and activation of gene expression.

Bromodomains are evolutionarily conserved 110-amino acid protein modules that recognize and bind to acetylated lysine residues (KAc) on histone proteins and regulate epigenetic information by turning genes on and off. Bromodomains were first reported in the Drosophila protein brahma, and are present in many chromatin-associated proteins and nearly all known nuclear histone acetyltransferases (HATs). Bromodomains play a role in chromatin remodeling, and function as acetyl-lysine binding domains. Lysine acetylation is dynamic, as this modification directs both structural changes to chromatin and gene transcription. Without wishing to be bound by theory, it is believed that bromodomain is the sole protein domain known to recognize acetyl-lysine residues on proteins.

Bromodomains can contribute to highly specific histone acetylation by tethering transcriptional HATs to specific chromosomal sites, and to the assembly and activity of multi-protein complexes of chromatin remodeling such as SAGA and NuA4. Bromodomain-containing proteins have been implicated in functions of cellular differentiation and transcriptional regulation.

There are 61 human bromodomains contained within 46 different proteins, with some proteins containing multiple bromodomains. As illustrated in FIG. 1, the bromodomain extra-C terminal domain (BET) family of proteins includes BRDT, BRD2, BRD3, and BRD4. These proteins have been implicated in the regulation of transcription and proliferation. Bromodomain and extraterminal domain proteins are epigenome readers that play a key role in gene expression by acting at the interface between chromatin remodeling and transcriptional regulation.

BRD4, originally named MCAP, binds preferentially to acetylated lysine residues found in histones (H3K14ac and H4 dual lysines K5 and K12 or K8 and K16) and non-histone proteins (RelA subunit of nuclear factor (NF)kB). BRD4 associates with acetylated chromatin throughout the cell cycle, and regulates transcription at targeted loci. BRD4 stimulates G1 gene transcription and promotes cell cycle progression to S-phase. BRD4 activation also predicts the survival of patients with breast cancer. Activation of BRD4 manipulates the response of tumors to their microenvironments in vivo, resulting in reduction of tumor growth and metastasis in mice. BRD4 has been implicated in differentiation of NUT-midline carcinoma, as well as skeletal muscle differentiation in association with MyoD and myogenin, and knockout of BRD4 in mice is embryonic lethal.

BRD4 heterozygotes display pre- and post-natal growth defects associated with a reduced proliferation rate. These mice also exhibit a variety of anatomical abnormalities such as head malformations, absence of subcutaneous fat, cataracts, and abnormal liver cells. In primary cell cultures, heterozygous cells also display reduced proliferation rates and moderate sensitivity to methyl methanesulfonate. Embryos nullizygous for BRD4 die shortly after implantation and are compromised in their ability to maintain an inner cell mass in vitro, indicating a role in fundamental cellular processes.

The chemical inhibition of BRD4 alters gene expression and results in reduced proliferation of cancerous cells. As a result, BET bromodomain proteins are being targeted for use in male contraception and in the treatment of NUT-Midline carcinoma, leukemia and other cancers, HIV, cardiac failure, inflammation, and viral infection.

Certain small molecules disrupt the interaction between bromodomains and acetylated lysines. One such molecule, known as JQ1, specifically inhibits the BET family of bromodomain proteins from interacting with chromatin. Evaluations of JQ1 have indicated that BET bromodomain proteins can be targeted for use in male contraception and in the treatment of human diseases including cancer, inflammation, and viral infection.

The BET antagonist JQ1 is a cell-permeable small molecule that binds competitively to acetyl-lysine recognition motifs, such as bromodomains. JQ1 is highly potent and specific to a subset of human bromodomains, having excellent shape complementarity with the acetyl-lysine binding cavity. Binding of JQ1 significantly increases the thermal stability of all the bromodomains of the BET bromodomain and extra-terminal family, while no significant stability shifts are detectable outside the BET family, indicating that JQ1 is highly selective.

JQ1 is a triazolothienodiazepine also known as (S)-tert-butyl 2-(4-(4-chlorophenyl)-2,3,9-trimethyl-6H-thieno[3,2-f][1,2,4]triazolo[4,3-a][1,4]diazepin-6-yl)acetate, and has the chemical structure depicted below as Formula I:

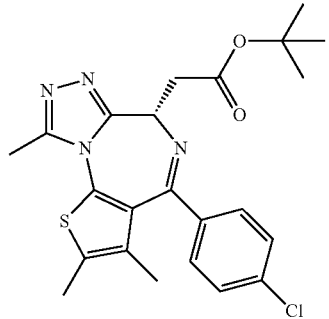

Formula I

It is to be understood that, unless otherwise specified, reference to "JQ1" herein can mean either one enantiomer or a racemic mixture of both enantiomers. The two JQ1 entantiomers, (+)-JQ1 and (−)-JQ1, are shown below as Formulas II and III, respectively:

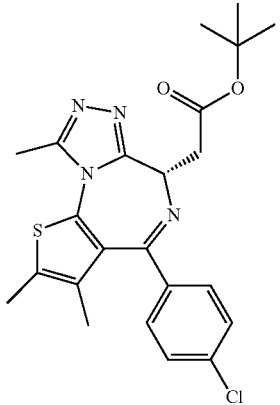

Formula II

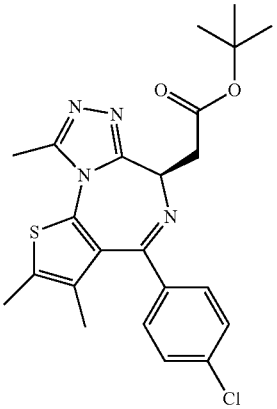

Formula III

Provided herein is a method for reducing pigment formation in melanocyte precursors (melanoblasts) and in differentiated melanocytes by exposing these cells to a BET bromodomain inhibitor, such as JQ1. Though JQ1 is discussed herein for illustrative purposes, it is to be understood that many other BET bromodomain protein inhibitors can be used in the method described herein, and the use of such other BET bromodomain protein inhibitors is entirely within the scope of the present disclosure. Suitable other BET bromodomain protein inhibitors include, but are not limited to: derivatives of JQ1; thienotriazolodiazepine compounds; inhibitor nucleic acid molecules such as siRNA, shRNA, or antisense nucleic acid molecules; compounds that bind in the binding pocket of the apo crystal structure of the first bromodomain of a BET family member; the compounds disclosed in U.S. Patent Application Publication 2010/0286127 (incorporated herein by reference); and the compounds disclosed in U.S. Patent Application Publication 2012/0157428 (incorporated herein by reference).

As shown in the examples described herein, JQ1 affects melanin production through two mechanisms. Without wishing to be bound by theory, JQ1 inhibits expression of genes that regulate melanin synthesis, and restrains proliferation by promoting cell cycle arrest. Therefore, topical administration of JQ1 is effective at treating hyperpigmentation disorders such as, but not limited to, melasma, solar lentigo, and lentigo senilis, which are characterized by excessive melanin production by melanocytes at localized areas of the skin. These disorders have localized regions of hyperpigmentation that result from increased melanin synthesis by melanocytes.

Treatment of melanoblasts and melanocytes with JQ1 inhibits proliferation, promotes cell cycle arrest, and inhibits the expression of tyrosinase, which is the rate-limiting enzyme for melanin, as well as two other enzymes (tyrosinase related protein 1 and dopachrome tautomerase) that regulate melanin synthesis. JQ1 inhibits TYR, TRP1, and DCT expression at both the protein and mRNA levels. The conventional treatment for hyperpigmentation, hydroquinone, results in skin lightening by inhibiting activity of tyrosinase—which is the rate-limiting enzyme in melanin synthesis—in melanocytes. Thus, treatment with JQ1 achieves skin lightening through a mechanism similar to hydroquinone.

As the examples herein show, the bromodomain protein BRD4 interacts with MITF, an important regulator of pigmentation and melanocyte proliferation, indicating that it is a target for modulation of pigmentation. BRD4 also mediates the effects of JQ1. Thus, pigmentation can be inhibited through the inhibition of BET bromodomain proteins by small molecules such as JQ1. This method is useful for the treatment of hyperpigmentation disorders including, but not limited to, melasma, lentigo senilis, solar lentigo, post-inflammatory hyperpigmentation, ephelides, and other disorders affecting melanocytes.

In certain embodiments, the method described herein can be combined with one or more conventional treatments for hyperpigmentation including, but not limited to: tyrosinase inhibitors such as hydroquinone, azelaic acid, kojic acid, and licorice extract; chemical peeling compounds such as salicylic acid and glycolic acid; topical retinoids such as retinoic acid, retinol (vitamin A), 13-cis-retinoic acid, 9-cis-retinoic acid, or any drug which inhibits the cytochrome $P_{450}$ enzymes which metabolize retinoic acid, in place of or in addition to retinoic acid; corticosteroids; photoprotection agents; bakuchiol compositions; and glutathione derivatives.

PHARMACEUTICAL COMPOSITIONS

The BET bromodomain protein inhibitors described herein can be incorporated into pharmaceutical compositions for use in the treatment of various diseases or disorders. In certain embodiments, JQ1 is especially useful in a pharmaceutical composition for the treatment of hyperpigmentation disorders.

A pharmaceutical composition as described herein may be formulated with any BET bromodomain inhibitor, plus any pharmaceutically acceptable excipients, diluents, or carriers. The compositions can be compressed into tablets, or formulated as elixirs or solutions for convenient oral administration or administration by intramuscular or intravenous routes. The compounds can be administered transdermally and may be formulated as sustained release dosage forms and the like.

The compounds, compositions, and formulations provided herein are useful for treating animals, such as humans, for various diseases. A method of treating a human patient according to the present disclosure includes the administration of an effective amount of a BET bromodomain inhibitor or pharmaceutical composition comprising a BET bromodomain inhibitor. The BET bromodomain inhibitors can be formulated into compositions which may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions, and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to about 50 mg in the case of parenteral or inhalation administration, and from about 25 to about 500 mg in the case of oral or rectal administration) of the compounds. Dosages from about 0.5 to about 300 mg/kg per day, preferably 0.5 to 20 mg/kg, of active ingredient may be administered although it will, of course, readily be understood that the amount of the compound actually to be administered will be determined by a physician, in light of all the relevant circumstances including the condition to be treated, the choice of compound to be administered, and the choice of route of administration. Therefore, the dosage ranges discussed herein are not intended to limit the scope of the present disclosure in any way.

The formulations useful for separate administration of the BET bromodomain inhibitors normally contain at least one compound selected from the compounds of a BET bromodomain inhibitor (which may be referred to herein as the active ingredient or active substance) mixed with a carrier, or diluted by a carrier, or enclosed or encapsulated by an ingestible carrier in the form of a capsule, sachet, cachet, paper, or other container, or by a disposable container such as an ampoule. A carrier or diluent may be a solid, semi-solid, or liquid material which serves as a vehicle, excipient, or medium for the active therapeutic substance. Some examples of the diluents or carriers which may be employed in the pharmaceutical compositions of the present disclosure are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol, and propellants such as trichloromonofluoromethane, dichlorodifluoromethane, and dichlorotetrafluoroethane. In the case of tablets, a lubricant may be incorporated to prevent sticking and binding of the powdered ingredients in the dies and on the punch of the tableting machine. For such purposes there may be employed, for instance, aluminum, magnesium, or calcium stearates, talc, or mineral oil.

In certain embodiments, pharmaceutical compositions of the present disclosure comprise an effective amount of a BET bromodomain inhibitor and/or additional agents, dissolved or dispersed in a pharmaceutically acceptable carrier. The phrases "pharmaceutical" or "pharmacologically acceptable" refer to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it will be understood that preparations should meet sterility, pyrogenicity, and general safety and purity standards as required by the FDA Office of Biological Standards.

A composition disclosed herein may comprise different types of carriers depending on whether it is to be administered in solid, liquid or aerosol form, and whether it needs to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and the route of administration. Depending upon the dosage and the route of administration, the number of administrations of a preferred dosage and/or an effective amount may vary according to the response of the subject. The compounds of the present disclosure are generally effective over a wide dosage range. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by those preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft- shell gelatin capsules, or they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,613,308, 5,466,468, 5,543,158; 5,641, 515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In certain cases the form should be sterile and should be fluid to the extent that easy injectability exists. It should be stable under the conditions of manufacture and storage and may optionally be preserved against the contaminating action of microorganisms, such as bacteria and fungi. The carrier can be a solvent or dispersion medium containing, for example, water, ethanol, a polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, such as, but not limited to, sugars or sodium chloride. Prolonged absorption of the injectable compositions can be brought about by the use in the compositions of agents delaying absorption such as, for example, aluminum monostearate, or gelatin.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. Sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream, and petrolatum as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the composition is in a form which is suitable for application to human skin. In certain embodiments, the composition is in the form of an oil, ointment, cream, lotion, or gel. In certain embodiments, the composition contains, as additional ingredients, any of: water, oil, alcohols (such as ethanol, isopropanol, or propanol), emulsifying agents, perfumes, coloring agents, fillers, abrasive agents, moisturizers, or combinations thereof.

In certain embodiments, the compositions are suitable for delivery by eye drops, intranasal sprays, inhalation, and/or other aerosol delivery vehicles. Methods for delivering compositions directly to the lungs via nasal aerosol sprays have been described in U.S. Pat. Nos. 5,756,353 and 5,804, 212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

Preferred pharmaceutical forms of the present disclosure are creams, lotions, ointments, capsules, tablets, and injectable solutions. Especially preferred are formulations for topical administration.

KITS

It is further intended the compounds or compositions disclosed herein could be packaged in the form of a kit containing multiple containers. Many embodiments of such kits are possible. By way of non-limiting example, a kit could include multiple components for a process of making a BET bromodomain inhibitor, or for treating a hyperpigmentation disorder. In certain embodiments, a kit comprises a first container housing a BET bromodomain protein inhibitor, and a second container housing a pharmaceutically acceptable carrier, diluent, or excipient. In certain embodiments, the BET bromodomain protein inhibitor comprises JQ1. Many other variations and embodiments of kits are envisioned.

The kits typically further include instructions for using the components of the kit to practice the subject methods, but do not need to include such instructions. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a CD-ROM, diskette, or flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Figure 2:
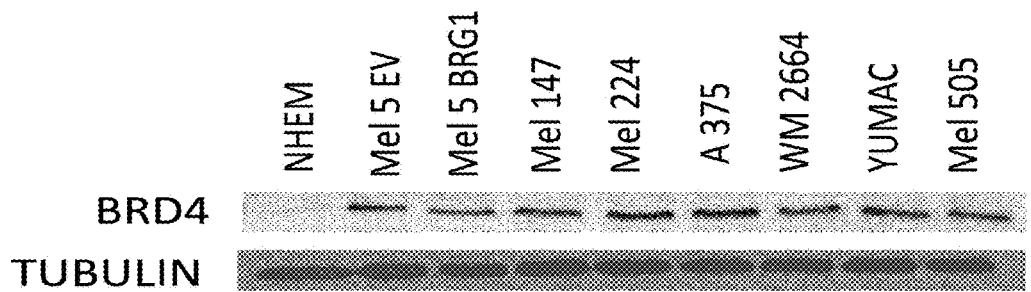
FIG. 2: Blot showing levels of BRD4 in melanocytes and melanoma cell lines.
Figure 3:
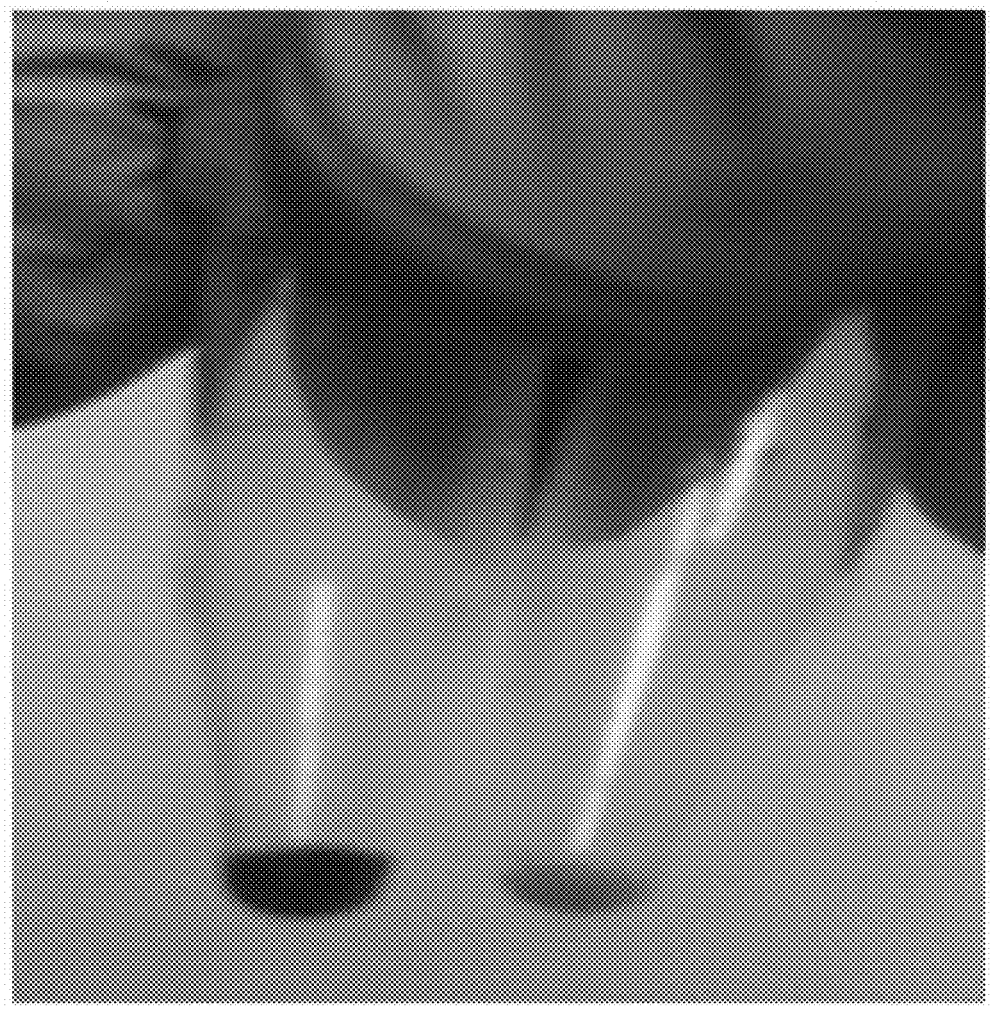
FIG. 3: Photograph showing mouse melanoblast (Melb-a) cells and Melb-a cells treated with JQ1. The test tube on the left contains Melb-a cells, and the test tube on the right contains Melb-a cells treated with 500 nM JQ1.
Figure 4A:
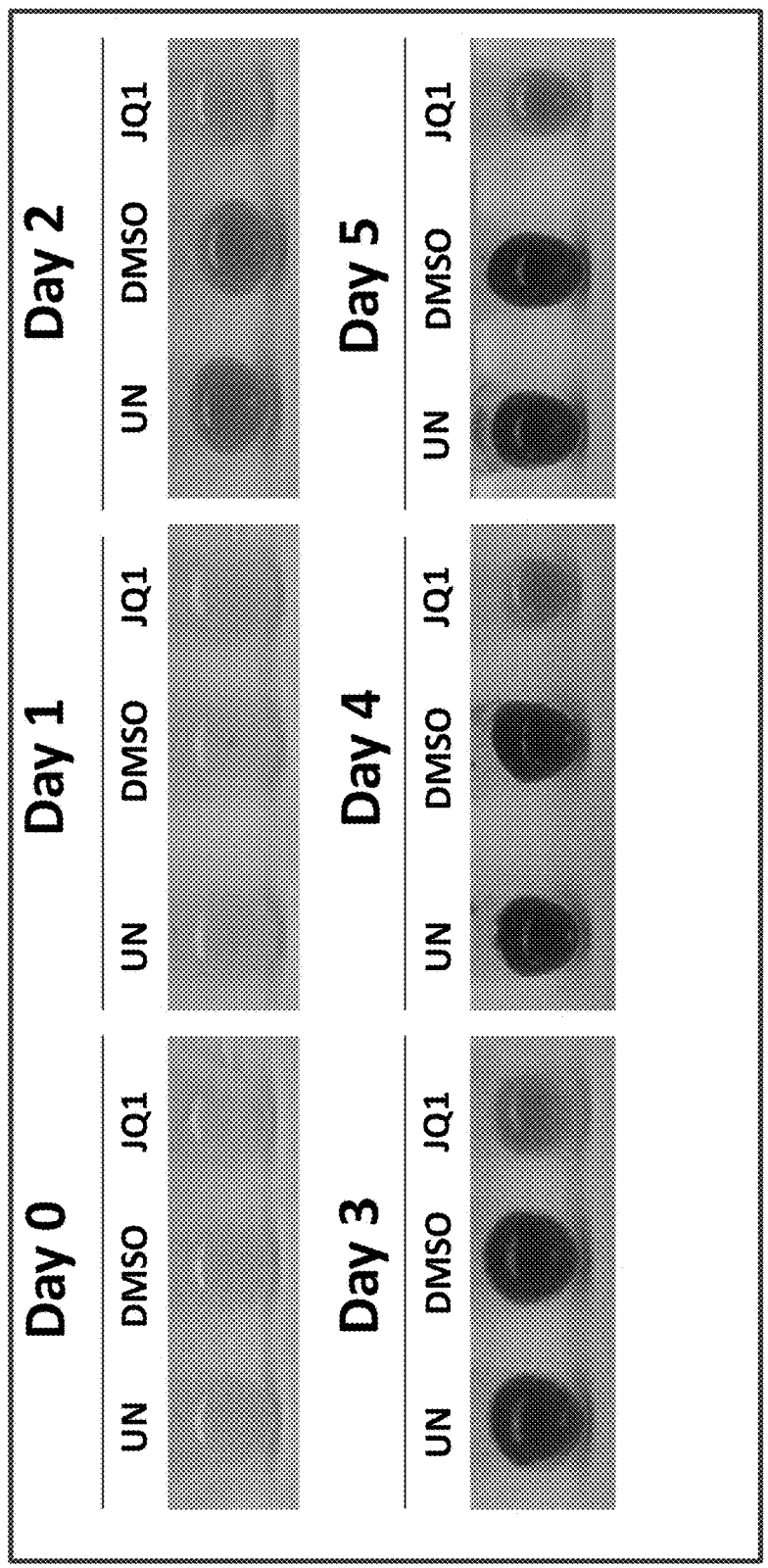
FIG. 4A: Mouse melanoblasts were differentiated in media containing α-melanocyte stimulating hormone (α-MSH) and Phorbol 12-myristate 13-acetate in the presence and absence of JQ1 (500 nM). JQ1 inhibited pigmentation two, three, four, and five days after treatment.

FIG. 2 shows the levels of BRD4 in melanocytes and melanoma cell lines. In order to demonstrate that targeting BET proteins can treat hyperpigmentation disorders, mouse melanocyte precursors were differentiated in the presence and absence of the BET protein inhibitor JQ1. An equal number of mouse melanoblasts expressing BRG1 and responsive to α-MSH were seeded onto polystyrene dishes and cultured in growth media. The growth media consisted of RPMI1640 (Life Technologies, Grand Island, N.Y.), 10% fetal calf serum (Life Technologies, Grand Island, N.Y.), 20 ng/ml stem cell factor, and 20 picoM fibroblast growth factor 2 at 37° C. When cells grew to cover 70% of the dish, they were shifted to differentiation media. The differentiation media consisted of DMEM (Life Technologies, Grand Island, N.Y.), 10% fetal calf serum, 200 nM phorbal 12-myristate 13-acetate (Sigma-Aldrich, St. Louis, Mo.) and 2 nM Nle4, D-Phe7-alpha-MSH (Sigma-Aldrich, St. Louis, Mo.). 500 nM JQ1 or vehicle (DMSO) was added to the cells that were maintained in growth media and to the cells that were shifted to differentiation media. (FIG. 3.) Cells were harvested at the time points indicated in FIG. 4A and photographed. As shown in the photographs of FIG. 4A, JQ1 inhibited melanin synthesis in cultured mouse melanoblasts.

Figure 4B:
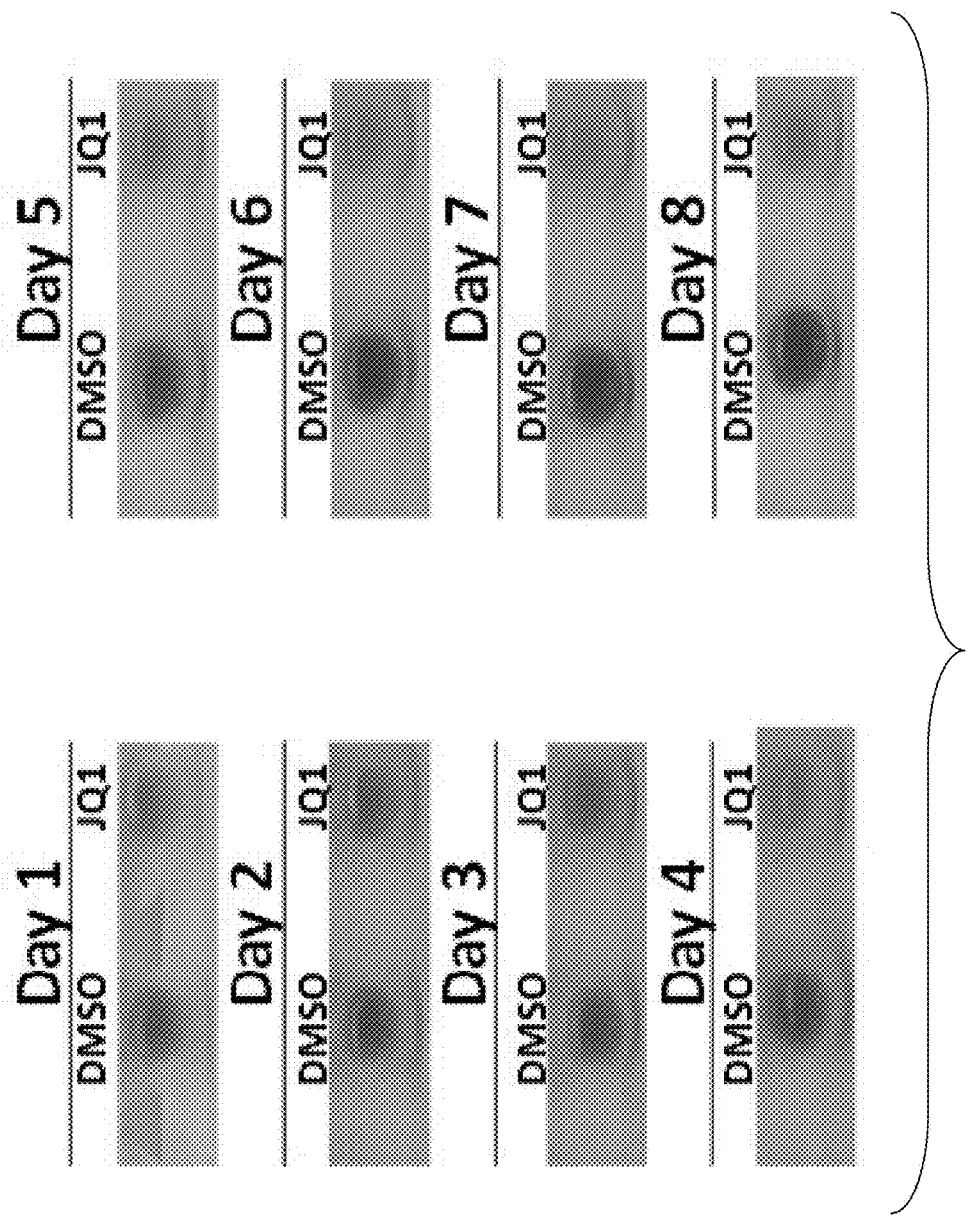
FIG. 4B: Neonatal human epidermal melanocytes were cultured in the presence and absence of JQ1 (500 nM) for 1-8 days. JQ1-treated melanocytes exhibited loss of pigmentation.

Human melanocytes were obtained from foreskins and cultured in the presence of 500 nM JQ1 or vehicle. Photographs were obtained at the time points indicated in FIG. 4B. As seen from FIG. 4B, treatment of human melanocytes with JQ1 resulted in depigmentation. The cells appeared smaller and less pigmented following JQ1 treatment.

Figure 5:
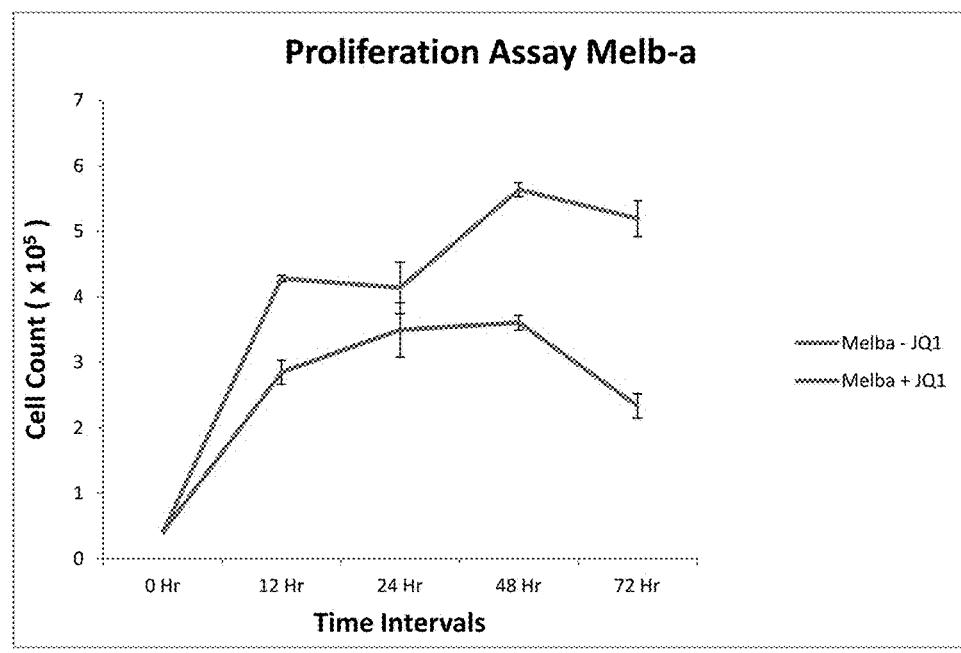
FIG. 5: Graph displaying the antiproliferative effect of JQ1 treatment on Melb-a cells.
Figure 6A:
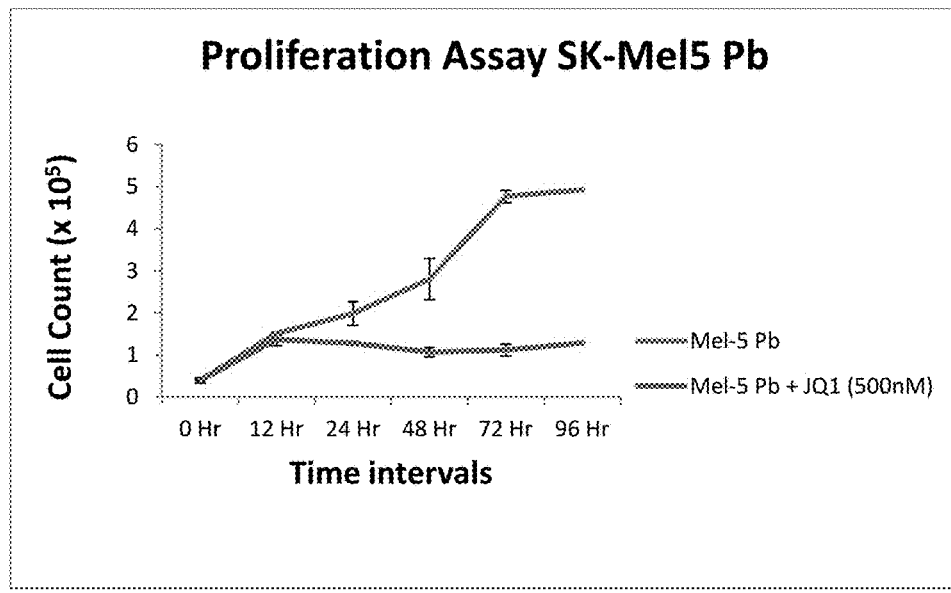
FIGS. 6A-6D: Results of proliferation assays displaying the effect of JQ1 treatment on melanoma cell lines. Cell counts of the melanoma cells decreased over time upon treatment with JQ1 compared to melanoma cells not treated with JQ1 or treated with the inactive isomer of JQ1 (−JQ1).
Figure 6A:
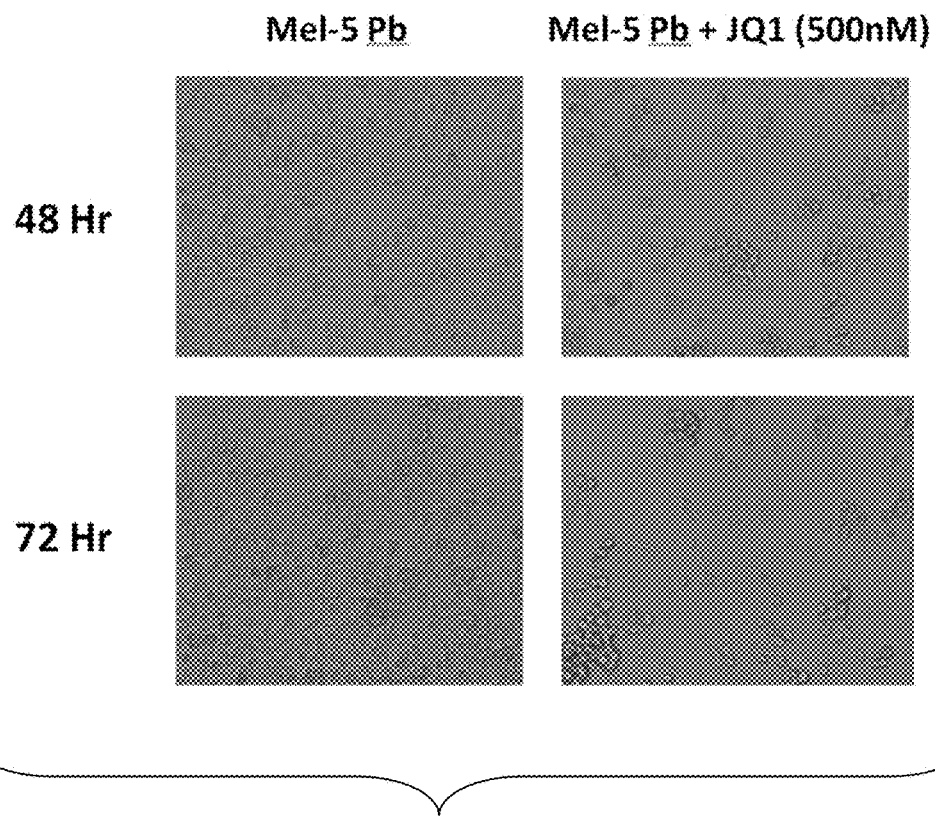
Figure 6B:
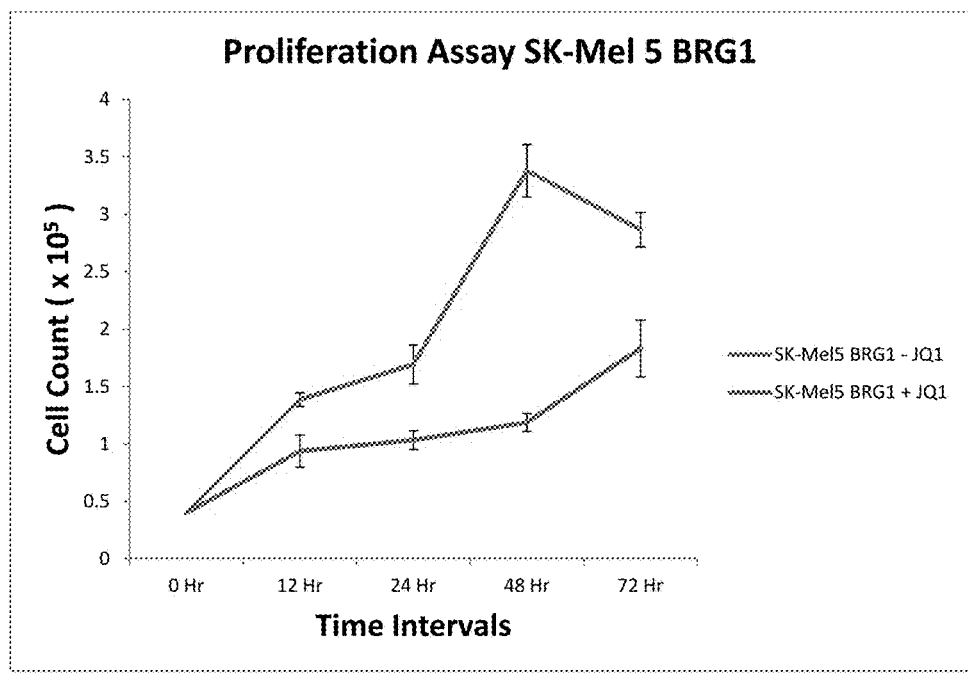
Figure 6C:
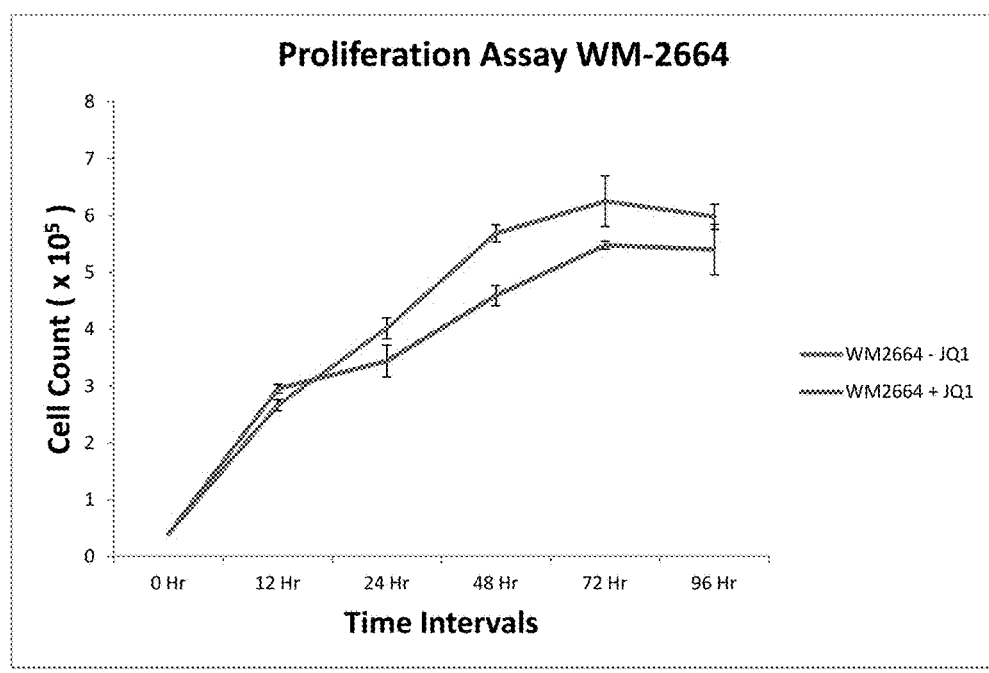
Figure 6D:
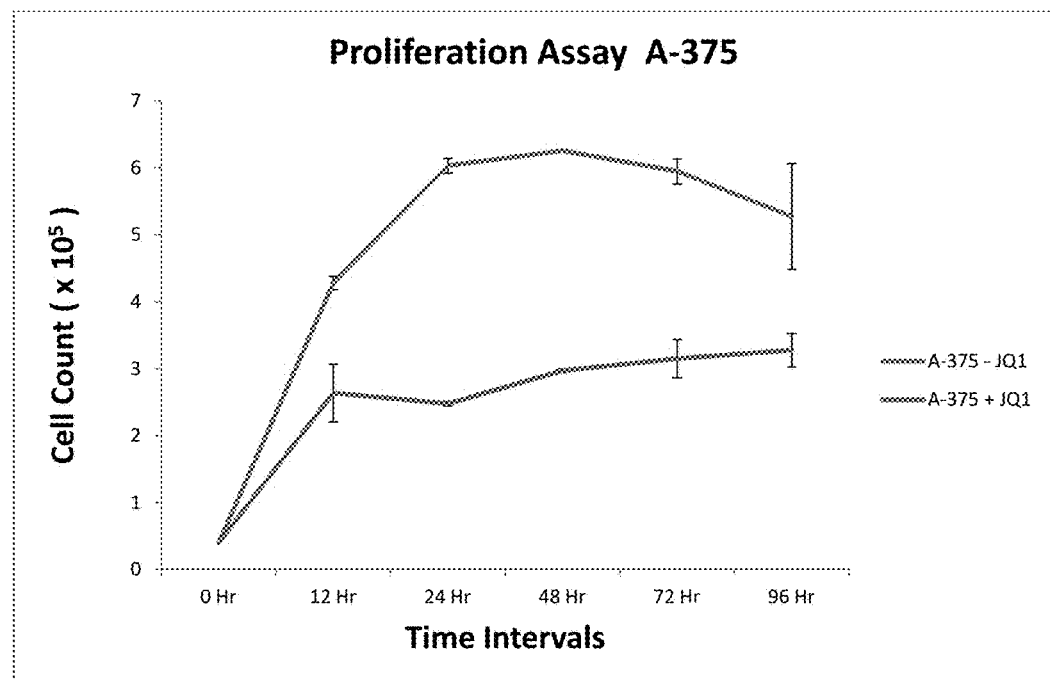

A proliferation assay was conducted to determine the antiproliferative effect of JQ1 treatment on Melb-a cells and melanoma cell lines. As shown in FIG. 5, no cell death was observed in JQ1-treated cells, ruling out the possibility of apoptosis. FIGS. 6A-6D show the effect of JQ1 treatment on melanoma cell lines.

Figure 7A:
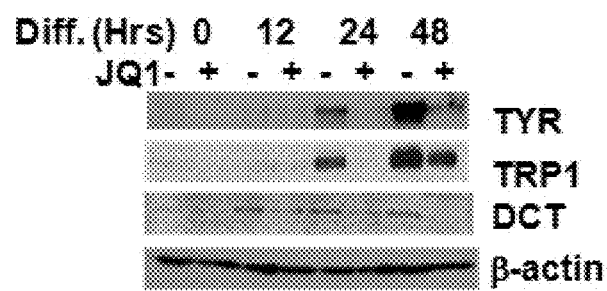
FIG. 7A: Western blot showing TYR, TRP1, and DCT protein levels in mouse melanoblasts that were differentiated in the presence or absence of JQ1. β-actin was a loading control. JQ1 substantially reduced TYR, TRP1, and DCT expression at the protein level.

To assay the effects of JQ1 on gene expression at the protein level, total cell extracts were prepared from cells at time points indicated in FIG. 7A and were subjected to Western blotting. Antibodies to detect TYR, TRP1, and DCT, and the loading control, β-actin, were from Santa Cruz Biotechnology (Santa Cruz, Calif.).

Figure 7B:
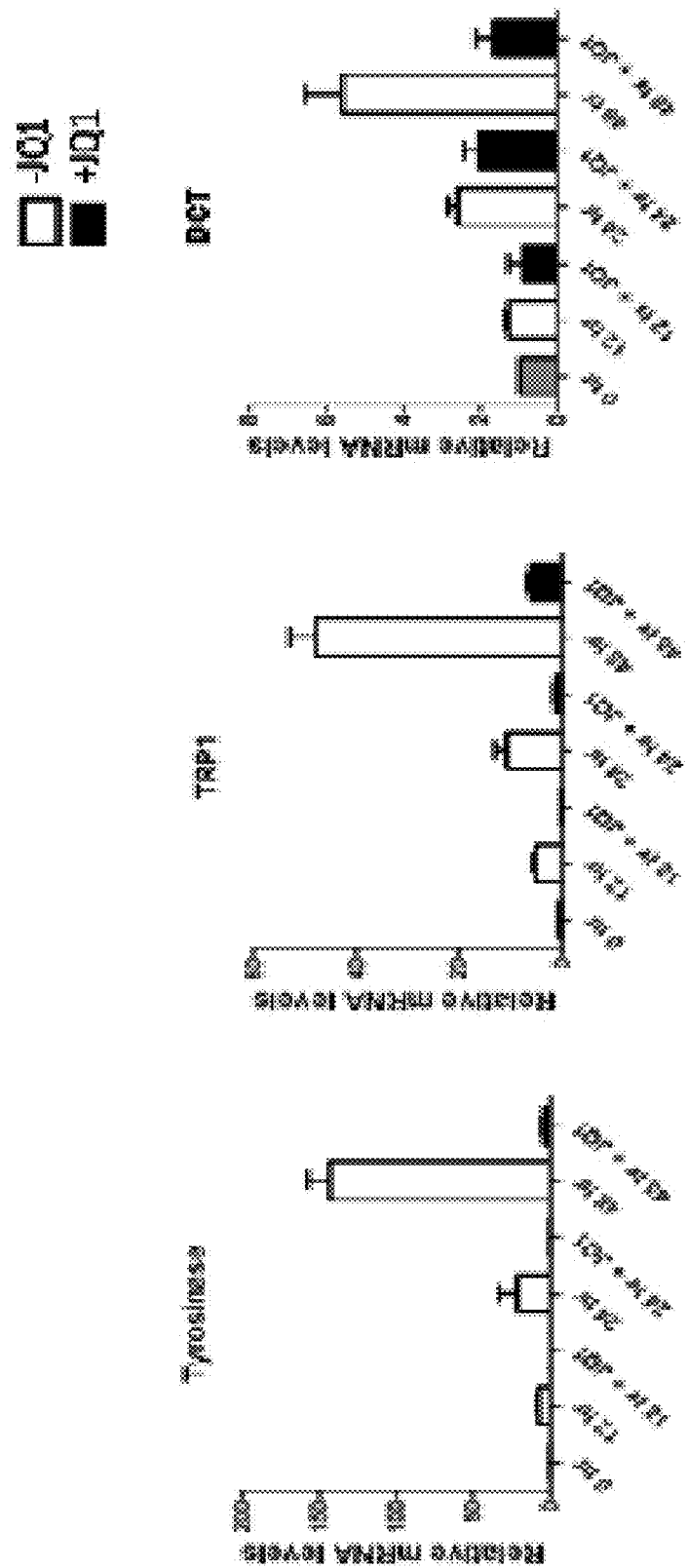
FIG. 7B: Quantitative PCR (qPCR) showing TYR, TRP1, and DCT mRNA levels in mouse melanoblasts that were differentiated in the presence or absence of JQ1 (500 nM). TYR, TRP1, and DCT mRNA levels were standardized to RPL7 mRNA levels. JQ1 significantly reduced TYR at the mRNA level.
Figure 8:
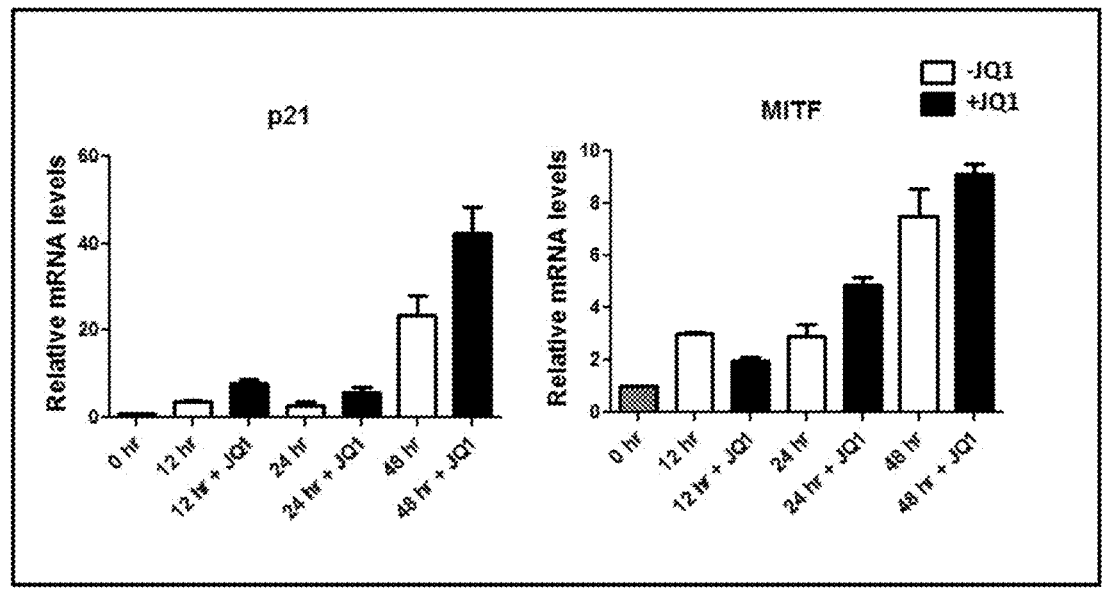
FIG. 8: Effect of JQ1 on p21 and MITF.
Figure 9:
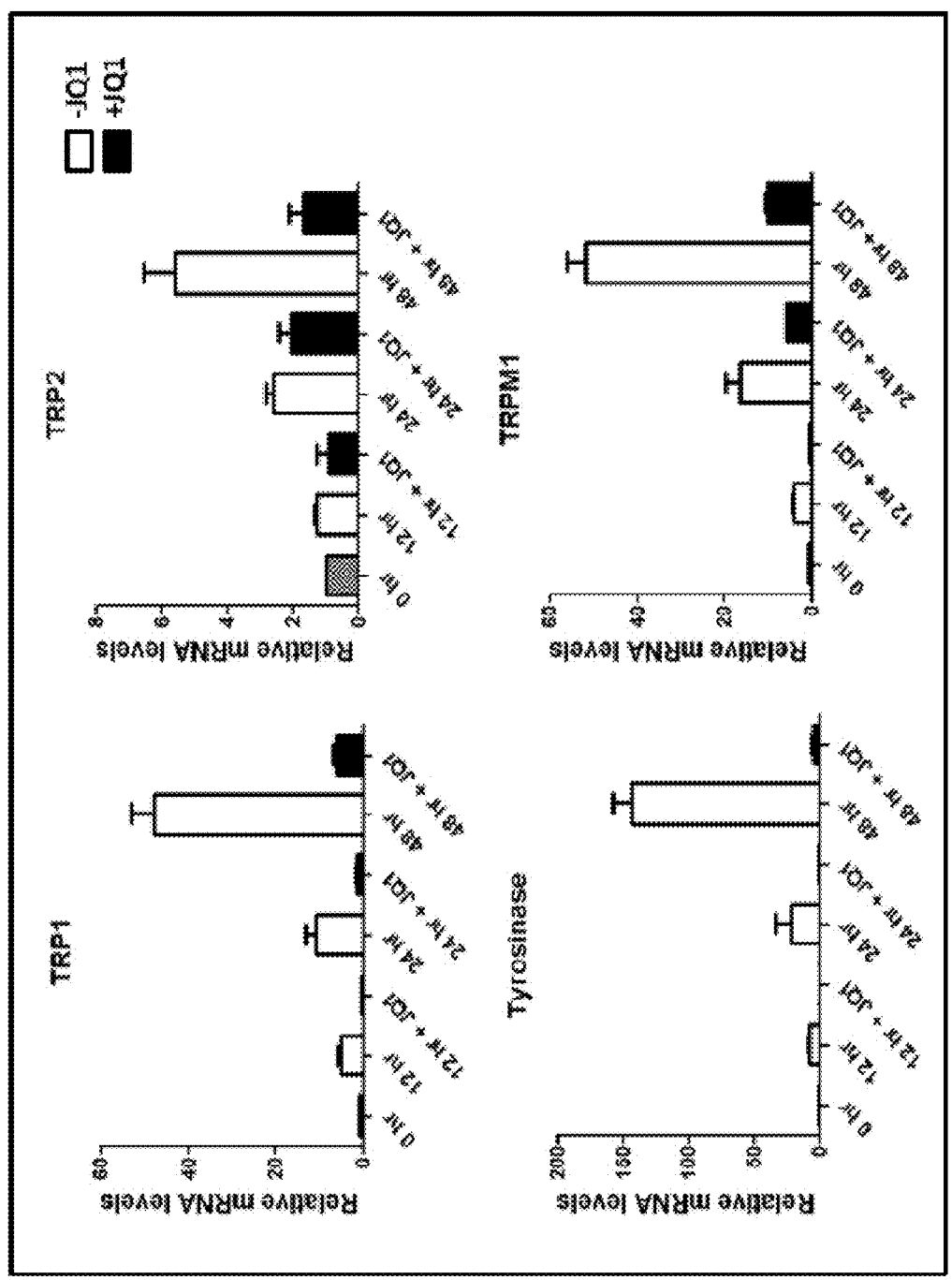
FIG. 9: JQ1 treatment inhibits differentiation.

To assay the effects of JQ1 on gene expression at the RNA level, RNA was isolated from cells at time points indicated in FIG. 7B, reverse-transcribed, and subjected to quantitative PCR. As seen from FIGS. 7B, 8, and 9, JQ1 inhibited expression of pigmentation genes.

To assay for physical interactions between BRD4 and MITF, 293T cells were transfected with epitope-tagged (FLAG) MITF using Lipofectomine LTX (Life Technologies, Grand Island, N.Y.).

Figure 7C:
FIG. 7C: Western blot demonstrating that microphthalmia-associated transcription factor (MITF) physically interacts with BRD4 in a co-immunoprecipitation experiment. This data establishes a link between BRD4 and the melanocyte specific transcription factor, MITF.

Total cell extracts were immunoprecipitated with an antibody to BRD4 and were subjected to Western blotting. The Western blot was probed with an antibody to BRD4 (Abcam, Cambridge, Mass.) and an antibody to the FLAG epitope (Sigma Aldrich, St. Louis, Mo.), as shown in FIG. 7C.

Figure 10A:
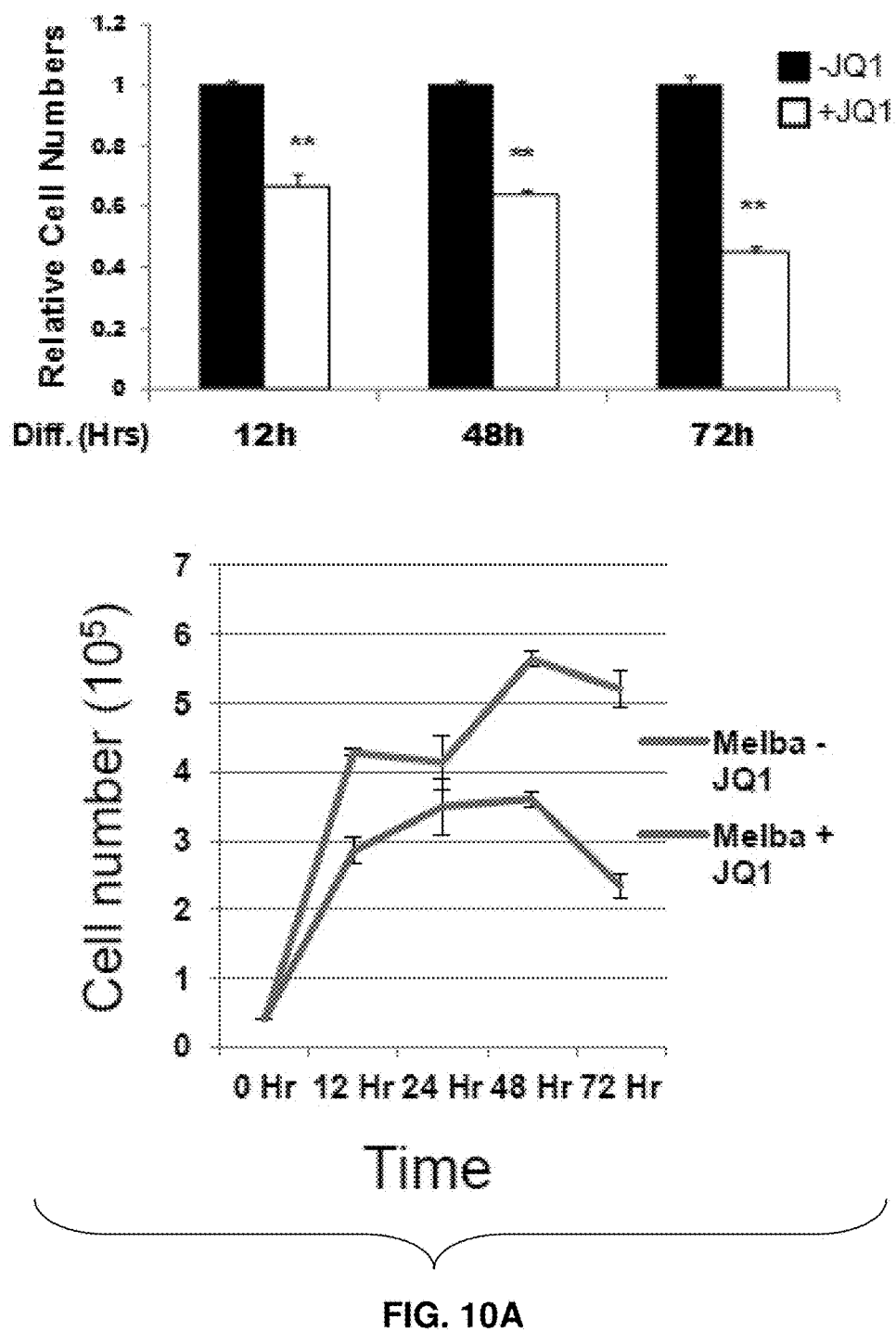
FIG. 10A: The effects of JQ1 (500 nM) on cell proliferation of melanoblasts that were differentiated in the presence or absence of JQ1 for the indicated time periods. JQ1 significantly suppressed proliferation.

In order to assess the effects of JQ1 (500 nM) on proliferation, cell counts were obtained after melanoblasts that were differentiated in the presence or absence of JQ1 for the indicated time periods. To determine the effects of JQ1 on cell proliferation, treated cells were harvested at the time points indicated in FIG. 10A and counted with a Scepter Hand-Held Automated Cell Counter (Millipore, Billerica, Mass.). JQ1 significantly suppressed proliferation.

Figure 10B:
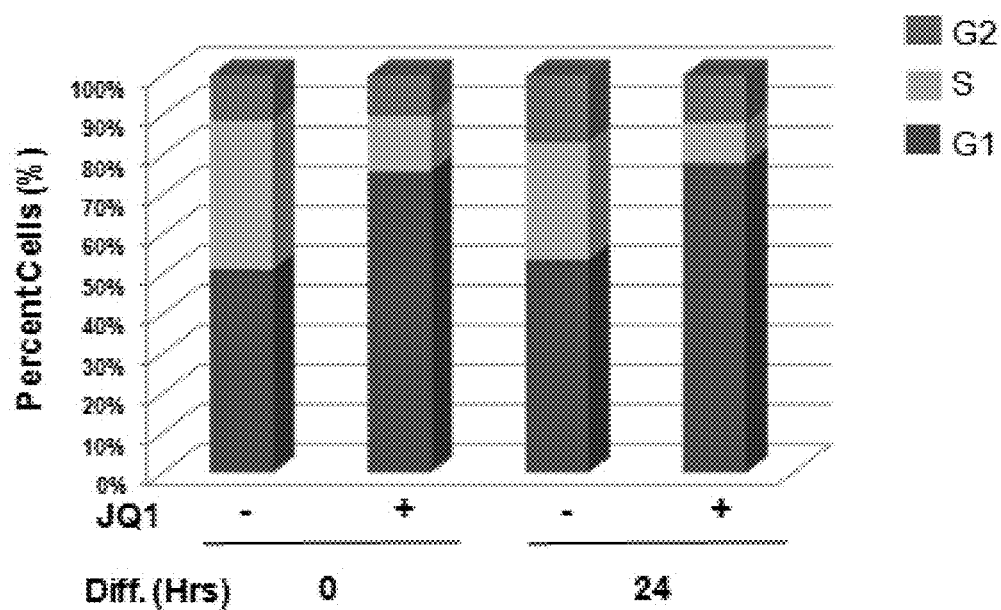
FIG. 10B: Flow cytometry results of propidium iodide staining of melanoblasts treated with JQ1 (500 nM). JQ1 promoted cell cycle arrest in G1.

To determine if the effects of JQ1 (500 nM) on proliferation were due to cell cycle changes, cells were stained with propidium iodide and subjected to flow cytometry. The effect of JQ1 on cell cycle regulation was determined by staining cells at the time points indicated in FIG. 10B with propidium iodide, and subjecting them to flow cytometry on a FACS-Calibur (BD Biosciences, San Jose, Calif., USA at the University of Toledo Flow Cytometry Core Facility). Data was analyzed using Cell Quest Pro (BD Biosciences). JQ1 promoted cell cycle arrest in G1.

Figure 11:
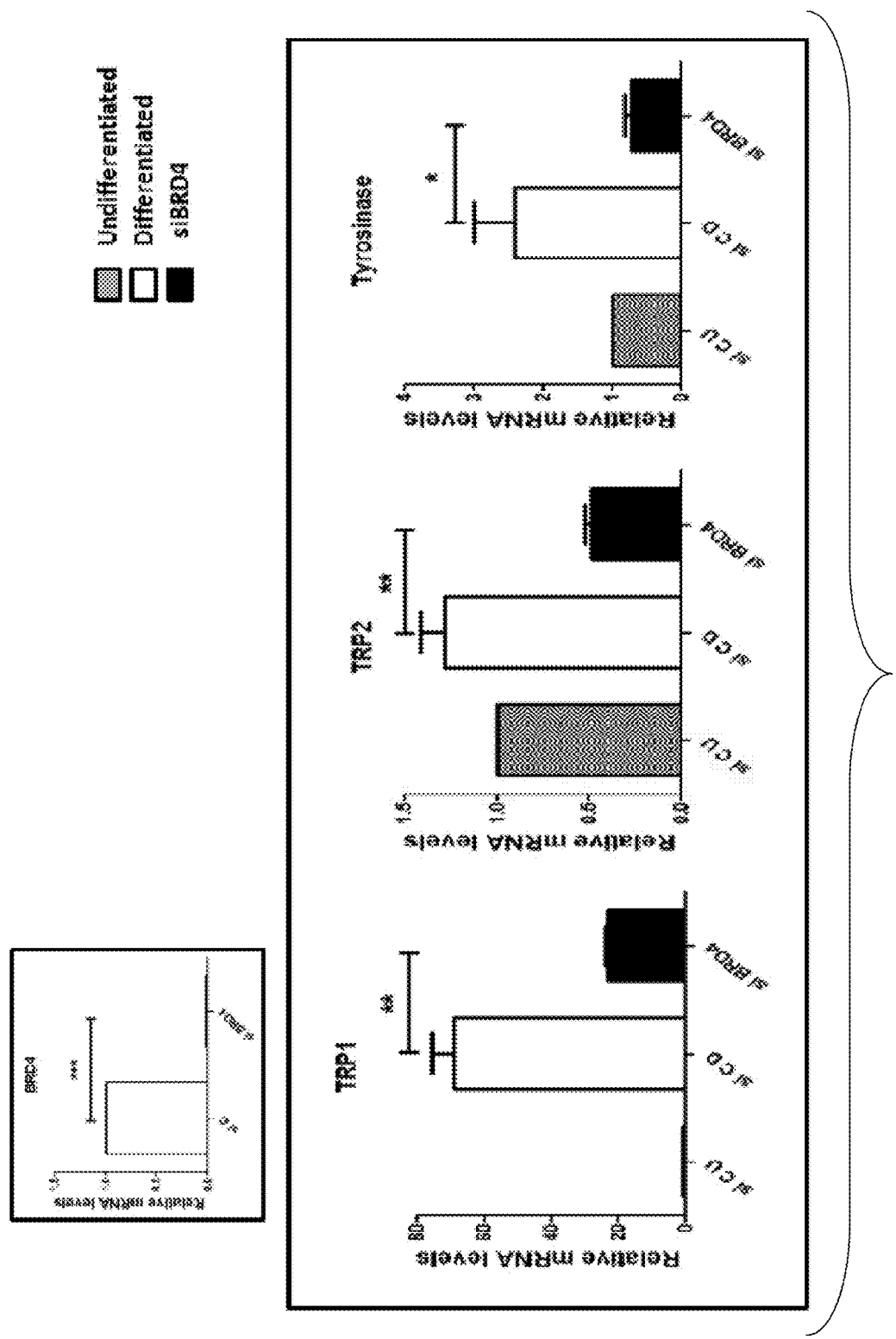
FIG. 11: BRD4 induces differentiation in Melb-a cells.

To determine if the effect of JQ1 is specific to BRD4, an RNA interference approach was utilized. The results (shown in FIG. 11) indicate that BRD4 induces differentiation in Melb-a cells.

Figure 12:
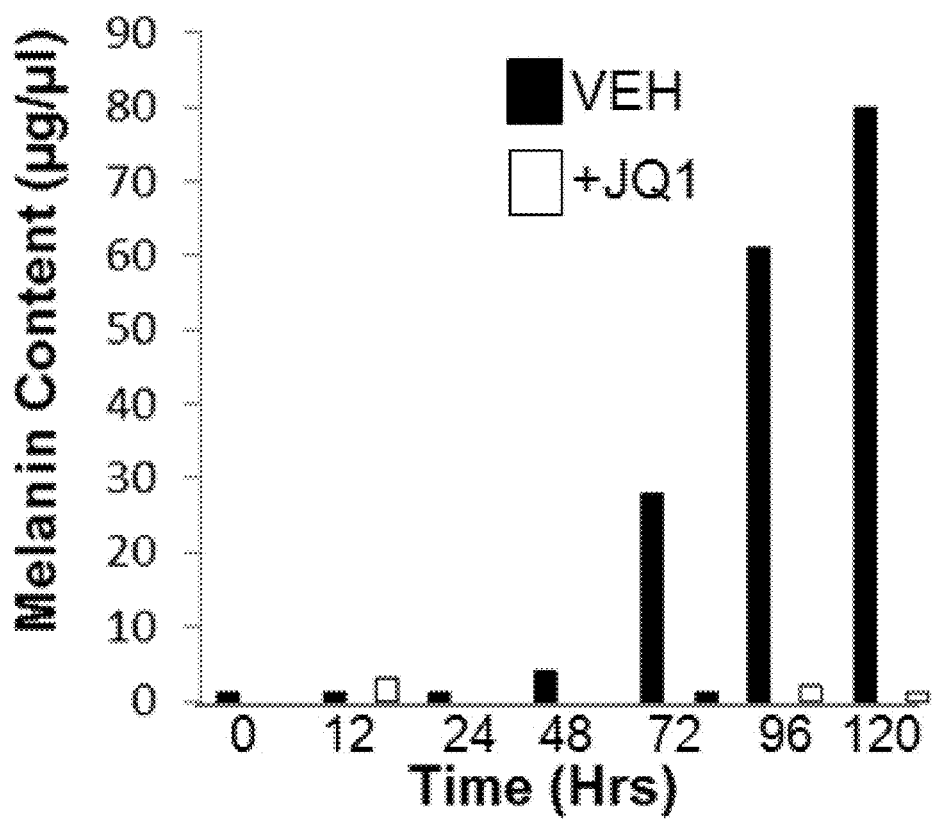
FIG. 12: Treatment of Melb-a cells with JQ1 inhibits melanin synthesis.

The melanin content of melanoblasts treated with JQ1 was analyzed. Melb-a melanoblasts were differentiated in the presence of JQ1 or vehicle and harvested at the time points indicated in FIG. 12. Equal numbers of cells from each plate were lysed in 0.1 M NaOH and vortexed for 20 minutes. Melanin content was calculated based on the absorbance at 475 nm as compared to melanin standards. The results are shown in FIG. 12. As seen in FIG. 12, the melanoblasts differentiated in the presence of JQ1 had significantly lower melanin content than the melanoblasts differentiated in the vehicle without JQ1.

Figure 13:
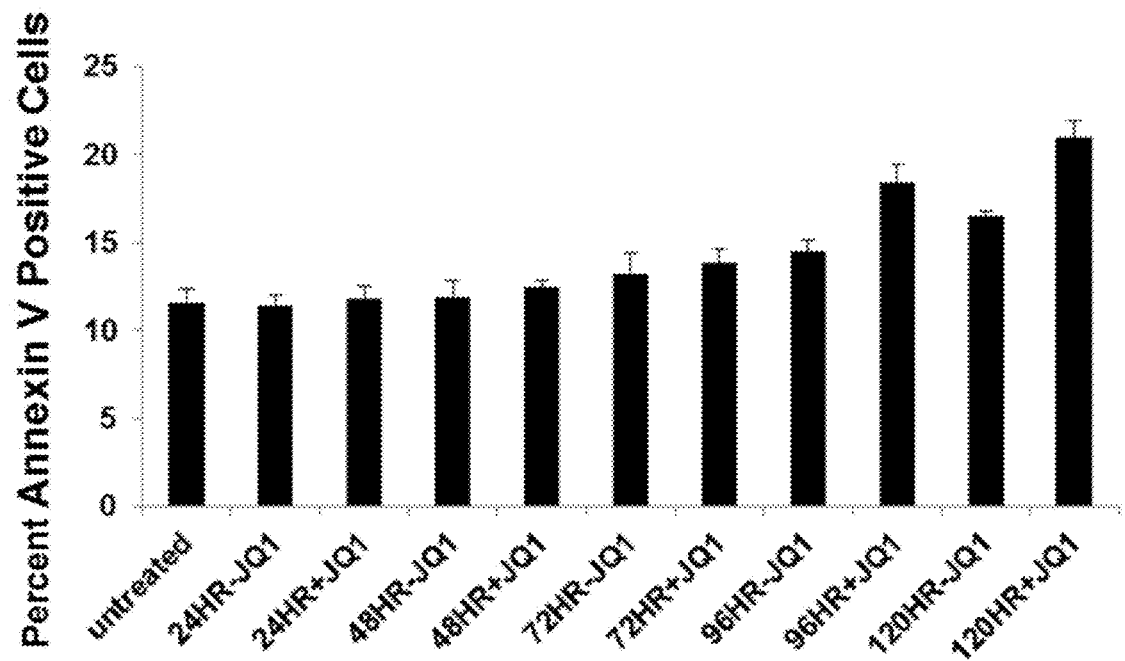
FIG. 13: Treatment of neonatal human epidermal melanocytes (NHEMs) with JQ1 results in very little apoptosis.

Neonatal human epidermal melanocyte (NHEM) cells were cultured in the absence of JQ1 (untreated), in the presence of an inactive isomer of JQ1 (−JQ1), or the active isomer of JQ1 (+JQ1), for the number of days indicated in FIG. 13. Cells were then stained with Annexin V and subjected to flow cytometry. Percent Annexin V positive cells indicate the percent of cells undergoing apoptosis. As seen from FIG. 13, the long term exposure of melanocytes to JQ1 resulted in minimal cell death.

Figure 14A:
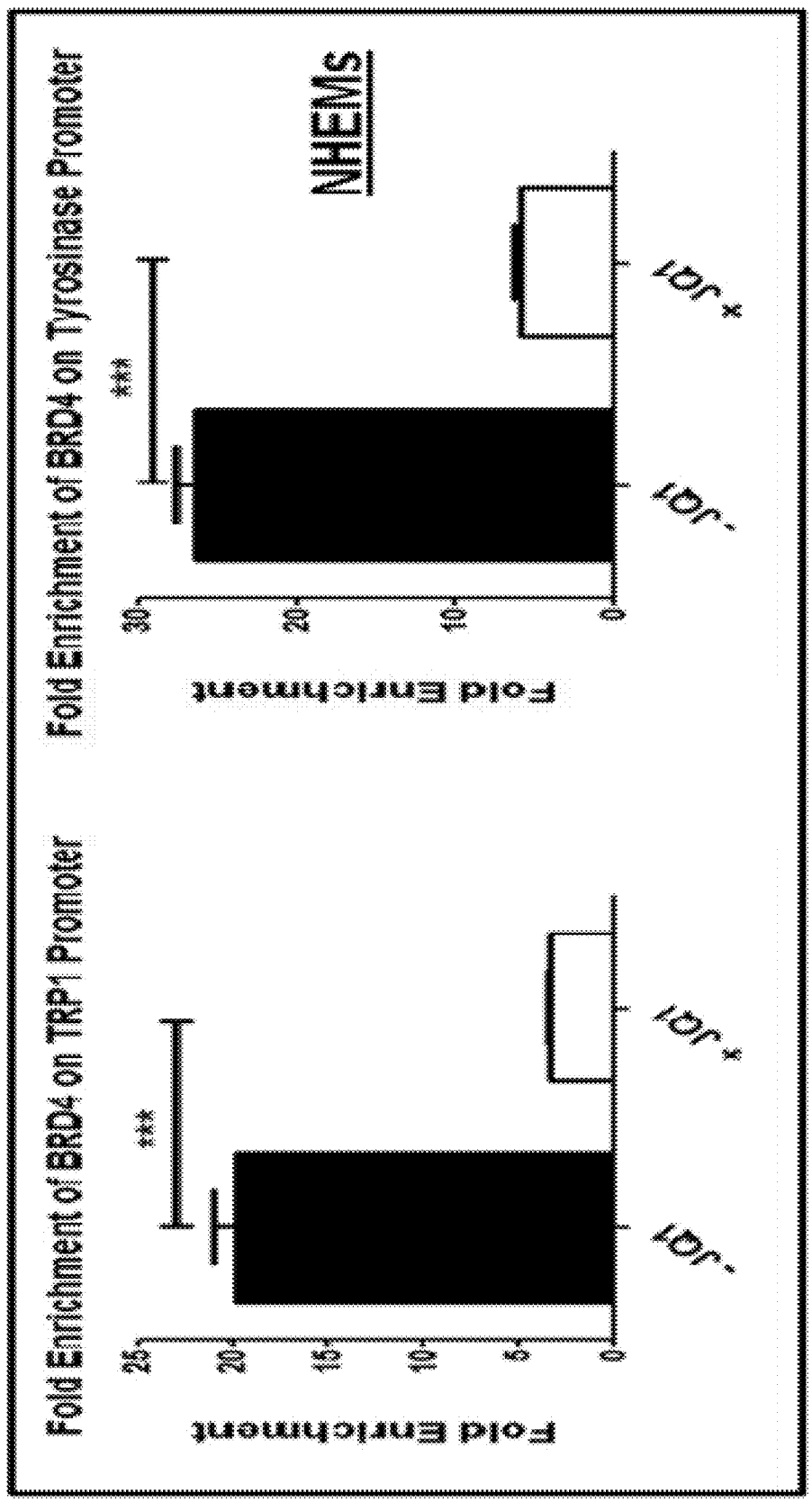
FIGS. 14A-14B: BRD4 occupancy of melanocyte specific promoters is disrupted when cells are cultured in JQ1.
Figure 14B:
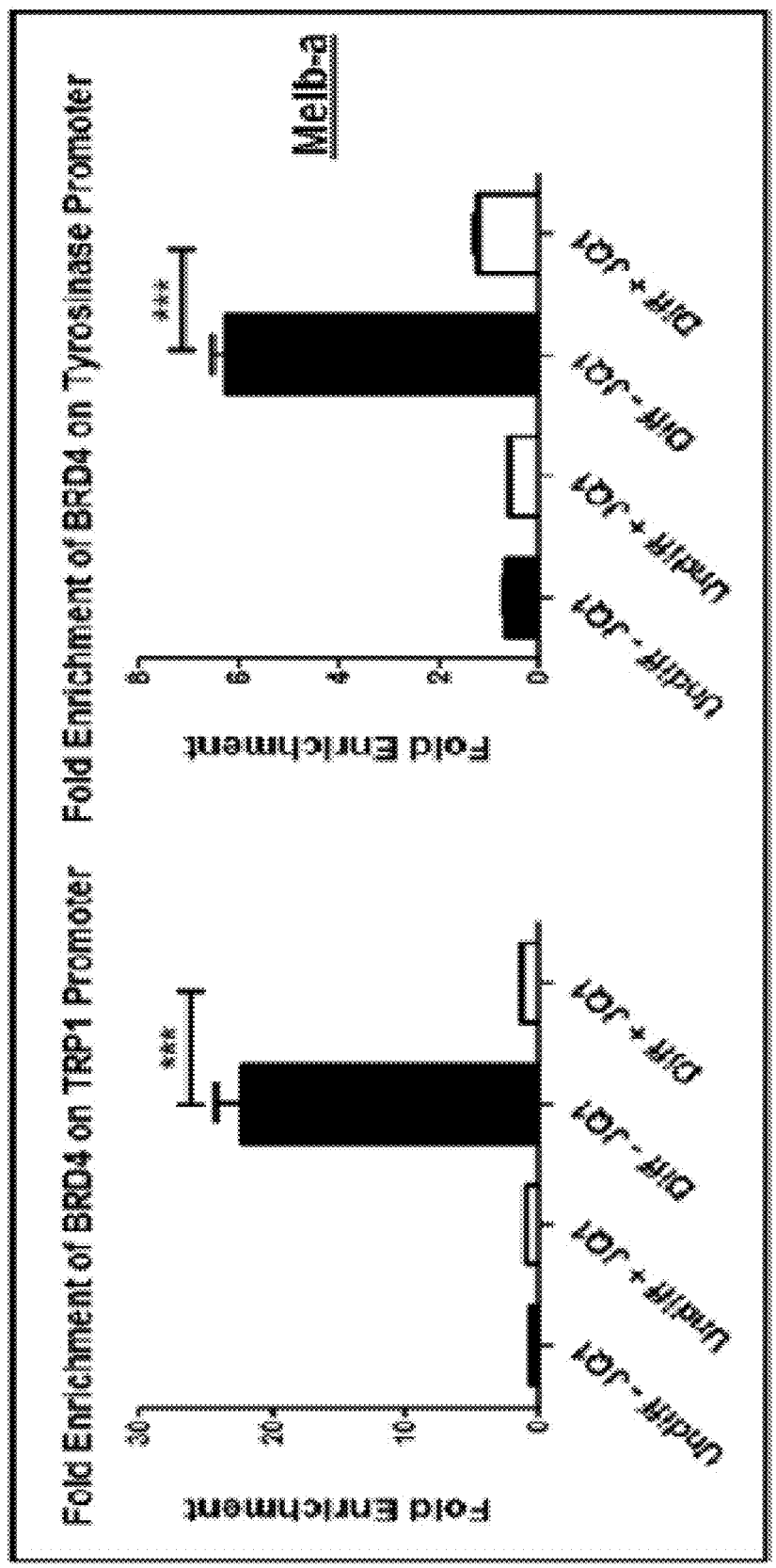

As shown in FIGS. 14, chromatin immunoprecipitations were performed with an antibody to BRD4 on NHEMs (FIG. 14A) or Melb-a (FIG. 14B) that were cultured in the presence of an inactive isomer of JQ1 (−JQ1) or presence of the active isomer of JQ1 (+JQ1). BRD4 enrichment was quantified by qPCR using primers to the indicated promoters. The results in FIGS. 14A-14B show that BRD4 occupancy of melanocyte specific promoters was disrupted when cells were cultured in JQ1.

Figure 15A:
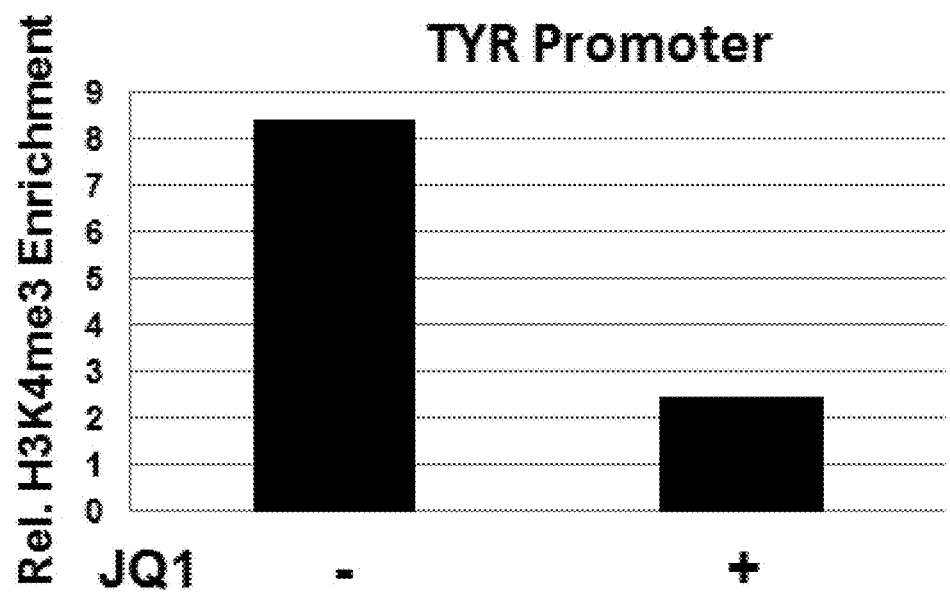
FIGS. 15A-15B: Treatment of Melb-a cells with JQ1 alters chromatin structure on melanocyte specific promoters.
Figure 15B:
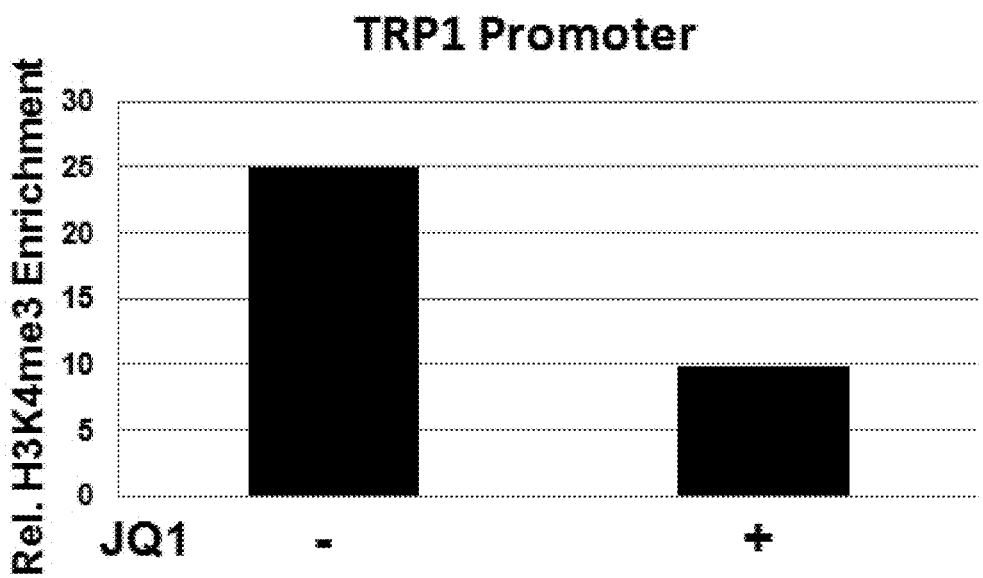

Chromatin immunoprecipitations were performed with an antibody to histone H3 trimethylated on lysine 4 (H3K4me3) on Melb-a cells that were cultured in the presence of the inactive isomer of JQ1 (−JQ1) or in the presence of the active isomer of JQ1 (+JQ1). H3K4me3 enrichment was quantified by qPCR using primers to the indicated promoters. H3K4me3 is a histone modification associated with active transcription. The results are shown in FIGS. 15A-15B. These data indicate that JQ1 disrupts this epigenetic mark; treatment of Melb-a cells with JQ1 altered chromatin structure on melanocyte specific promoters.

As shown in these examples, treatment with JQ1 dramatically decreased melanin synthesis in differentiating melanoblasts. Furthermore, treatment of neonatal human melanocytes with JQ1 resulted in the loss of melanin. The effect of JQ1 on melanin synthesis was associated with decreased expression of tyrosine, the rate-limiting enzyme required for melanin synthesis, as well as decreased expression of two enzymes that regulate the type of melanin produced: tyrosinase related protein 1 and dopachrome tautomerase. JQ1 also inhibited melanocyte proliferation by promoting G1 cell cycle arrest. JQ1 treatment had an antiproliferative effect on Melb-a cells as well as melanoma cell lines. Furthermore, long term exposure to JQ1 was shown to result in minimal cell death. In addition, down-regulation of differentiation-specific genes was observed on JQ1 treatment. The BET protein BRD4 was found to physically interact with MITF, the master regulator of melanocyte differentiation and a protein required for melanocyte-specific gene expression and melanocyte proliferation. Additionally, BRD4 was found to induce differentiation of Melb-a cells. In total, these results demonstrate that BRD4 plays an important role in melanocyte differentiation by interacting with MITF, and can be targeted by BET protein inhibitors for the treatment of hyperpigmentation disorders.

Certain embodiments of the methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of reducing pigmentation in a skin cell comprising:
    administering an effective amount of a BET bromodomain protein inhibitor to a skin cell to reduce pigmentation in the skin cell,
    wherein the BET bromodomain protein inhibitor comprises a triazolothienodiazepine also known as (S)-tert-butyl 2-(4-(4-chlorophenyl)-2,3,9-trimethyl-6H-thieno[3,2-f][1,2,4]triazolo[4,3-a][1,4]diazepin-6-yl)acetate, having the chemical structure of Formula I:

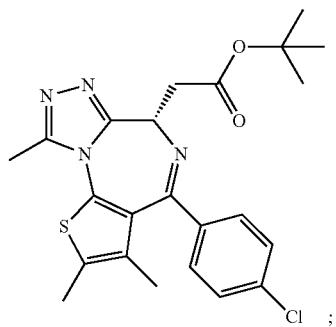

Formula I wherein the BET bromodomain protein inhibitor is administered at a dosage of about 500 nM.

2. The method of claim 1, wherein the BET bromodomain protein inhibitor has the chemical formula of Formula II:

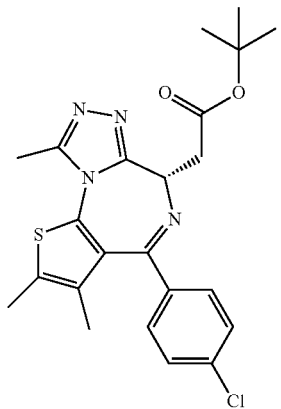

Formula II

3. The method of claim 1, wherein pigment formation in melanocytes is reduced.

4. The method of claim 1, wherein pigment formation in melanocyte precursors is reduced.

5. The method of claim 1, wherein the skin cell is a melanoma cell.

6. The method of claim 1, wherein the BET bromodomain protein inhibitor is administered in the form of an ointment, cream, or lotion.

7. A method of treating a hyperpigmentation disorder comprising:
    administering an effective amount of a BET bromodomain protein inhibitor to a patient in need thereof, and treating a hyperpigmentation disorder,
    wherein the BET bromodomain protein inhibitor comprises, a triazolothienodiazepine also known as (S)-tert-butyl 2-(4-(4-chlorophenyl)-2,3,9-trimethyl-6H-thieno[3,2-f][1,2,4]triazolo[4,3-a][1,4]diazepin-6-yl)acetate, having the chemical structure of Formula I:

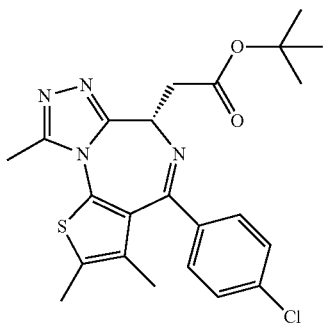

Formula I wherein the BET bromodomain protein inhibitor is administered at a dosage of about 500 nM.

8. The method of claim 7, wherein the hyperpigmentation disorder is selected from the group consisting of: melasma, lentigo senilis, solar lentigo, post-inflammatory hyperpigmentation, and ephelides.

9. The method of claim 7, wherein the administering comprises applying a topical composition to human skin.

10. The method of claim 7, further comprising administering an additional treatment for a hyperpigmentation disorder, wherein the additional treatment is selected from the group consisting of: hydroquinone, azelaic acid, kojic acid, licorice extract, salicylic acid, glycolic acid, retinoic acid, retinol, 13-cis-retinoic acid, 9-cis-retinoic acid, corticosteroids, photoprotection agents, bakuchiol compositions, glutathione derivatives, and combinations thereof.

11. The method of claim 7, wherein the BET bromodomain protein inhibitor is administered in the form of an ointment, cream, or lotion.

12. A method of reducing melanin content in a cell, the method comprising:
administering an effective amount of a BET bromodomain protein inhibitor to a cell, and reducing melanin content in the cell,
wherein the BET bromodomain protein inhibitor comprises, a triazolothienodiazepine also known as (S)-tert-butyl 2-(4-(4-chlorophenyl)-2,3,9-trimethyl-6H-thieno[3,2-f][1,2,4]triazolo[4,3-a][1,4]diazepin-6-yl)acetate, having the chemical structure of Formula I:

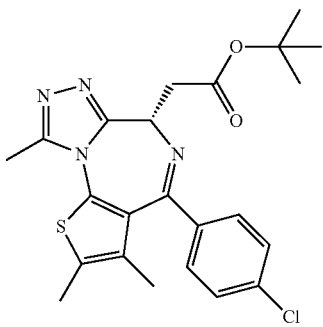

Formula I wherein the BET bromodomain protein inhibitor is administered at a dosage of about 500 nM.

13. The method of claim 12, wherein the cell is a melanoblast.

14. A method of suppressing melanocyte proliferation comprising:
administering an effective amount of a BET bromodomain protein inhibitor to melanocytes, and suppressing proliferation of the melanocytes,
wherein the BET bromodomain protein inhibitor comprises, a triazolothienodiazepine also known as (S)-tert-butyl 2-(4-(4-chlorophenyl)-2,3,9-trimethyl-6H-thieno[3,2-f][1,2,4]triazolo[4,3-a][1,4]diazepin-6-yl)acetate, having the chemical structure of Formula I:

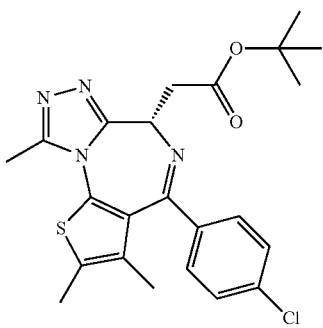

Formula I wherein the BET bromodomain protein inhibitor is administered at a dosage of about 500 nM.

15. The method of claim 14, wherein the melanocytes comprise melanoma cells.

* * * * *